(12) United States Patent
Liu et al.

(10) Patent No.: US 9,481,827 B2
(45) Date of Patent: Nov. 1, 2016

(54) CORE-SHELL NANOPARTICLE AND METHOD OF GENERATING AN OPTICAL SIGNAL USING THE SAME

(71) Applicants: Agency for Science, Technology and Research, Singapore (SG); National University of Singapore, Singapore (SG)

(72) Inventors: Xiaogang Liu, Singapore (SG); Weifeng Yang, Singapore (SG); Renren Deng, Singapore (SG)

(73) Assignees: Agency for Science, Technology and Research, Singapore (SG); National University of Singapore, Singapore (SG)

( * ) Notice: Subject to any disclaimer, the term of this patent is extended or adjusted under 35 U.S.C. 154(b) by 0 days.

(21) Appl. No.: 14/932,119

(22) Filed: Nov. 4, 2015

(65) Prior Publication Data
US 2016/0122635 A1    May 5, 2016

(30) Foreign Application Priority Data

Nov. 4, 2014 (SG) .......................... 10201407230W

(51) Int. Cl.
| | | |
|---|---|---|
| *G01T 1/04* | (2006.01) | |
| *C09K 11/77* | (2006.01) | |
| *G01N 21/64* | (2006.01) | |
| *G01J 1/58* | (2006.01) | |

(52) U.S. Cl.
CPC ............ *C09K 11/7704* (2013.01); *C09K 11/77* (2013.01); *C09K 11/7772* (2013.01); *C09K 11/7773* (2013.01); *G01J 1/58* (2013.01); *G01N 21/64* (2013.01); *G01N 21/6428* (2013.01)

(58) Field of Classification Search
CPC ....... G01J 1/58; G01N 21/64; G01N 21/6428; C09K 11/77
USPC ............................................ 250/473.1, 459.1
See application file for complete search history.

(56) References Cited

U.S. PATENT DOCUMENTS

| 8,093,566 B2* | 1/2012 | Zhang ............... A61K 41/0071 250/459.1 |
|---|---|---|
| 2007/0254981 A1* | 11/2007 | DiMaio ................... C09K 11/02 523/200 |
| 2008/0176076 A1* | 7/2008 | van Veggel ...... A61K 47/48861 428/404 |
| 2012/0064134 A1* | 3/2012 | Bourke, Jr. ............ A61Q 17/04 424/401 |

FOREIGN PATENT DOCUMENTS

CN          104109531        * 10/2014   ............ C09K 11/02

\* cited by examiner

*Primary Examiner* — David Porta
*Assistant Examiner* — Meenakshi Sahu
(74) *Attorney, Agent, or Firm* — Winstead, P.C.

(57) ABSTRACT

A core-shell nanoparticle is provided. The core-shell nanoparticle has a core comprising a metal fluoride doped with a first sensitizer and a shell surrounding the core, wherein the shell comprises a first layer comprising the metal fluoride doped with a second sensitizer and a first activator, and a second layer comprising the metal fluoride doped with a third sensitizer and a second activator, wherein the first activator and the second activator are different, and each is independently selected from the group consisting of $Tm^{3+}$, $Ho^{3+}$, and combinations thereof. A method of generating an optical signal using the core-shell nanoparticle and a method of preparing the core-shell nanoparticle is also provided.

20 Claims, 5 Drawing Sheets

(A)

(B)

(A)

(B)

CORE-SHELL NANOPARTICLE AND METHOD OF GENERATING AN OPTICAL SIGNAL USING THE SAME

CROSS-REFERENCE TO RELATED APPLICATION

This application claims the benefit of priority of Singapore patent application No. 10201407230W filed on 4 Nov. 2014, the content of which is incorporated herein by reference in its entirety for all purposes.

TECHNICAL FIELD

Various embodiments relate to a core-shell nanoparticle, a method of generating an optical signal using the core-shell nanoparticle, and a method of preparing the core-shell nanoparticle.

BACKGROUND

The development of luminescent materials or luminophores with multi-color emission is important for biological studies requiring multiplex bio-markers. In conventional design, the multi-color emission was mainly achieved by adjusting internal composition of the luminescent materials. Unfortunately, application of the luminescent materials is limited in that one specific luminophore is only able to emit one emission color under a single wavelength of excitation.

In view of the above, there is a need for an improved material that overcomes or at least alleviates one or more of the above-mentioned problems, such as by possessing ability to exhibit multiple colors under a single excitation wavelength.

SUMMARY

In a first aspect, a core-shell nanoparticle is provided. The core-shell nanoparticle has a core comprising a metal fluoride doped with a first sensitizer and a shell surrounding the core, wherein the shell comprises a) a first layer comprising the metal fluoride doped with a second sensitizer and a first activator, and b) a second layer comprising the metal fluoride doped with a third sensitizer and a second activator, wherein the first activator and the second activator are different, and each is independently selected from the group consisting of $Tm^{3+}$, $Ho^{3+}$, and combinations thereof.

In a second aspect, a method of generating an optical signal is provided. The method comprises a) irradiating a core-shell nanoparticle with radiation, the core-shell nanoparticle having a core comprising a metal fluoride doped with a first sensitizer and a shell surrounding the core, wherein the shell comprises i. a first layer comprising the metal fluoride doped with a second sensitizer and a first activator, and ii. a second layer comprising the metal fluoride doped with a third sensitizer and a second activator, wherein the first activator and the second activator are different, and each is independently selected from the group consisting of $Tm^{3+}$, $Ho^{3+}$, and combinations thereof; and b) controlling at least one of a wavelength or a duration of the radiation to generate the optical signal from the core-shell nanoparticle.

In a third aspect, a method of preparing a core-shell nanoparticle is provided. The method comprises a) providing a nanoparticle comprising a metal fluoride doped with a first sensitizer, and b) forming a shell having a first layer comprising the metal fluoride doped with a second sensitizer and a first activator and a second layer comprising the metal fluoride doped with a third sensitizer and a second activator on the nanoparticle, wherein the first activator and the second activator are different, and each is independently selected from the group consisting of $Tm^{3+}$, $Ho^{3+}$, and combinations thereof.

BRIEF DESCRIPTION OF THE DRAWINGS

The invention will be better understood with reference to the detailed description when considered in conjunction with the non-limiting examples and the accompanying drawings, in which.

DETAILED DESCRIPTION

Figure 1:
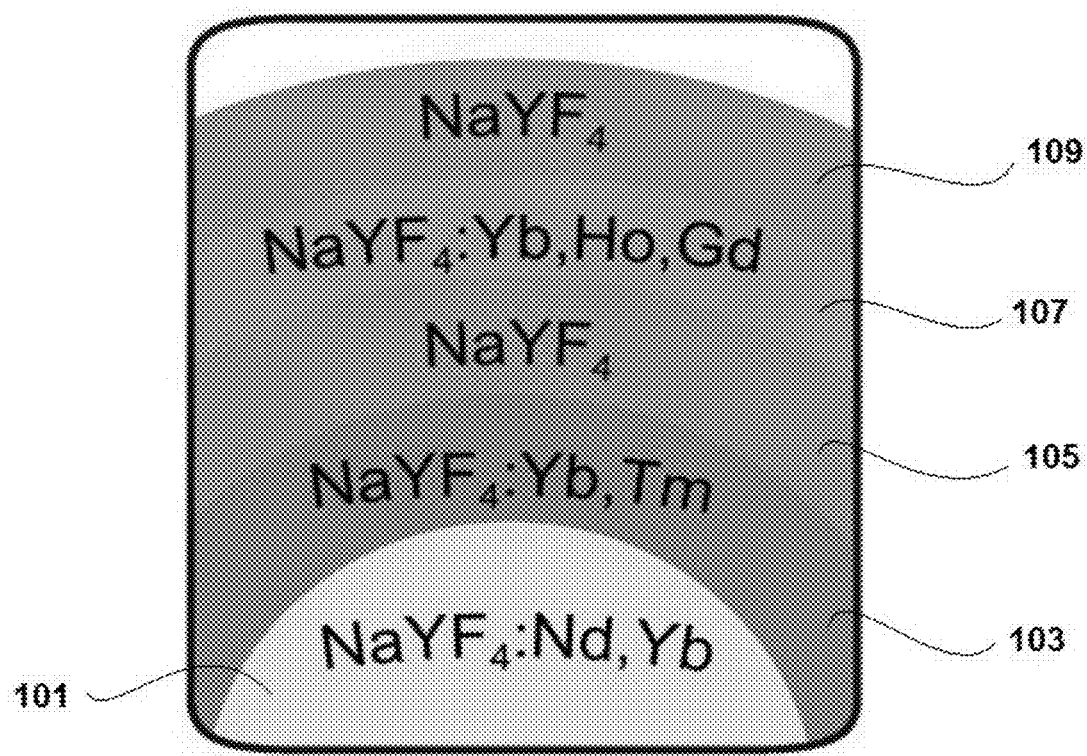
FIG. 1 is a schematic diagram depicting a sodium yttrium fluoride ($NaYF_4$) nanocrystal having a multilayer core-shell structure according to an embodiment, in which different lanthanide metals are doped in specific core/shell layers. In the figure, core 101 contains $NaYF_4$ doped with neodymium (Nd) and ytterbium (Yb); first layer 103 contains $NaYF_4$ doped with ytterbium (Yb) and thulium (Tm); second layer 105 contains $NaYF_4$; third layer 107 contains $NaYF_4$ doped with ytterbium (Yb), holmium (Ho) and gadolinium (Gd); fourth layer 109 contains $NaYF_4$.

As disclosed herein, a core-shell nanoparticle is provided. The core-shell nanoparticle may be used for multi-color emission whereby light of various colors may be obtained from a single core-shell nanoparticle by controlling the excitation conditions at which the core-shell nanoparticle is subjected to. In contrast to conventional luminophores in which a single luminophore is only able to emit a single color, a core-shell nanoparticle disclosed herein is able to emit multiple colors through varying at least one of a wavelength or a duration of an incident radiation. In various embodiments, the core-shell nanoparticle is able to emit visible emission with high brightness, high photostability, wide color gamut, and excellent color saturation under near-infrared light excitation via a photon upconversion process.

The term "photon upconversion" as used herein refers to a process in which two or more photons of lower energy are sequentially absorbed and results in emission of a single photon having a higher energy (shorter wavelength) than any of the absorbed photons. During photon upconversion, sequential absorption of two or more photons of low energy by a material may promote an electron from a ground state to an intermediate state and subsequently to an excited state. The electron may subsequently be radiatively relaxed from the excited state to the ground state by emitting a photon of high energy. In various embodiments, low energy laser stimulations may be converted via photon upconversion into high energy luminescent emissions.

The terms "nanoparticle" and "nanocrystal" are used interchangeably herein to refer to a nanoscopic particle having a size measured in nanometres (nm). The term "core-shell nanoparticles" refers to a structural configuration of nanoparticles in which an external layer formed of a second material encompasses an inner core of a first material, thereby forming the core-shell structure.

The core-shell nanoparticle may have a regular shape such as a nanosphere or be irregularly shaped, and size of the core-shell nanoparticle may be characterized by its diameter. The term "diameter" as used herein refers to the maximal length of a straight line segment passing through the center of a figure and terminating at the periphery. Although the term "diameter" is used normally to refer to the maximal length of a line segment passing through the centre and connecting two points on the periphery of a nanosphere, it is also used herein to refer to the maximal length of a line segment passing through the centre and connecting two points on the periphery of a nanoparticle having other shapes, such as a nanocube or a irregularly shaped nanoparticle.

In various embodiments, the core-shell nanoparticle has a diameter of 100 nm or less. For example, the core-shell nanoparticle may have a diameter in a range of about 10 nm to about 90 nm, about 10 nm to about 70 nm, about 10 nm to about 50 nm, about 10 nm to about 40 nm, about 20 nm to about 90 nm, about 40 nm to about 90 nm, about 60 nm to about 90 nm, about 30 nm to about 70 nm, about 40 nm to about 60 nm, or in a range of about 20 nm to 80 nm.

The core of the core-shell nanoparticle comprises a metal fluoride doped with a first sensitizer. In this regard, the metal fluoride may function as a host material or a host lattice to allow exchange of energy with dopant ions such as that of the first sensitizer contained within the metal fluoride. Accordingly, choice of the metal fluoride may determine distance and spatial position between the dopant ions. Advantageously, metal fluorides are chemically the most stable, and have low phonon energies to prevent non-radiative energy loss and to maximize radiative emission, which may translate into high luminescence efficiency of the resulting core-shell nanoparticle.

The metal fluoride may, for example, be a fluoride of Na, K, Ca, Y, Sr, Ba, Zr and Ti. In various embodiments, the metal fluoride is selected from the group consisting of $NaYF_4$, $CaF_2$, $NaGdF_4$, $NaLuF_4$ and combinations thereof. In specific embodiments, the metal fluoride comprises or consists of $NaYF_4$.

The metal fluoride in the core of the nanoparticle is doped with a first sensitizer. The term "sensitizer" as used herein refers to a substance which may be added to a host material to enhance or to suppress a characteristic of a dopant. In embodiments disclosed herein, the metal fluoride host material may be doped with a sensitizer to facilitate and/or to enhance energy transfer from radiation irradiated on the core-shell nanoparticle to an activator present in the core-shell nanoparticle, such as in the shell of the core-shell nanoparticle. In doping the metal fluoride, some of the atoms of the metal fluoride host lattice may be replaced by the first sensitizer.

In various embodiments, the first sensitizer comprises or consists of a lanthanide element. The lanthanide element may provide intermediate electronic states to allow energy of a low energy photon to be stored until a next low-energy photon arrives. Furthermore, lanthanide elements may have partially forbidden electronic transitions, which means that excited states of lanthanide ions may have life-times of up to several milliseconds. Consequently, the first sensitizer may absorb incident photons, and the absorbed energy may be transferred through a series of steps resonantly to an activator present in the core-shell nanoparticle to emit the upconverted radiation.

In various embodiments, the first sensitizer may be selected from the group consisting of lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), and combinations thereof.

The first sensitizer may be present in the metal fluoride in the form of ions. In some embodiments, the first sensitizer is selected from the group consisting of $Yb^{3+}$, $Nd^{3+}$, and combinations thereof. In specific embodiments, the first sensitizer comprises at least one of $Yb^{3+}$ or $Nd^{3+}$. Advantageously, $Yb^{3+}$ and $Nd^{3+}$ have large absorption cross sections, with $Yb^{3+}$ at 980 nm and $Nd^{3+}$ at 800 nm, which render their suitability for use as sensitizers. In applications which involve use of the core-shell nanoparticles in biological applications, however, $Nd^{3+}$ may be used in preference to $Yb^{3+}$, as the absorption of $Yb^{3+}$ ions may largely overlap the absorption band of water molecules that are dominant in biological samples. Consequently, the 980 nm excitation may be significantly attenuated while passing through biological samples. Moreover, overexposure of biological species to 980 nm irradiation may cause overheating issues to result in significant cell death and tissue damage.

The core of the core-shell nanoparticle may be doped uniformly with the first sensitizer. For example, distribution of the first sensitizer ions within the metal fluoride host material in the core may be at least substantially homogeneous.

Generally, size of the core of the core-shell nanoparticle is not particularly limited, and may be of any suitable size that renders diameter of the core-shell nanoparticle to 100 nm or less. For example, diameter of the core of the core-shell nanoparticle may be in the range of about 5 nm to about 97 nm, such as about 10 nm to about 95 nm, about 10 nm to about 90 nm, about 10 nm to about 75 nm, about 10 nm to about 60 nm, about 10 nm to about 50 nm, about 10 nm to about 30 nm, about 10 nm to about 20 nm, about 20 nm to about 95 nm, about 30 nm to about 90 nm, about 40 nm to about 60 nm, or about 30 nm to about 80 nm.

A shell surrounds the core of the core-shell nanoparticle. In various embodiments, the shell completely encompasses or encapsulates the core. The shell comprises a first layer comprising the metal fluoride doped with a second sensitizer and a first activator, and a second layer comprising the metal fluoride doped with a third sensitizer and a second activator.

As mentioned above, the metal fluoride may act as a host material to allow exchange of energy with dopant ions contained within the metal fluoride. Advantageously, the shell of the core-shell nanoparticle contains the same metal fluoride as that of the core, such that by using different dopant ions in the core and in the shell layers, optical signals, which may be in the form of one or more wavelengths in a range from about 380 nm to about 780 nm, may be selectively emitted from the core-shell nanoparticle.

As used herein, the term "activator" refers to a substance which is able to emit a photon. The first activator and the second activator comprised in the core-shell nanoparticle are different, and each is independently selected from the group consisting of $Tm^{3+}$, $Ho^{3+}$, and combinations thereof.

In various embodiments, the first activator comprises $Tm^{3+}$, which may emit blue light, while the second activator comprises $Ho^{3+}$, which may emit green and red light. By controlling at least one of a wavelength or a duration of radiation to the core-shell nanoparticle, optical signal which may be in the form of one or more wavelengths in a range from about 380 nm to about 780 nm may be selectively emitted from the core-shell nanoparticle.

Figure 4:
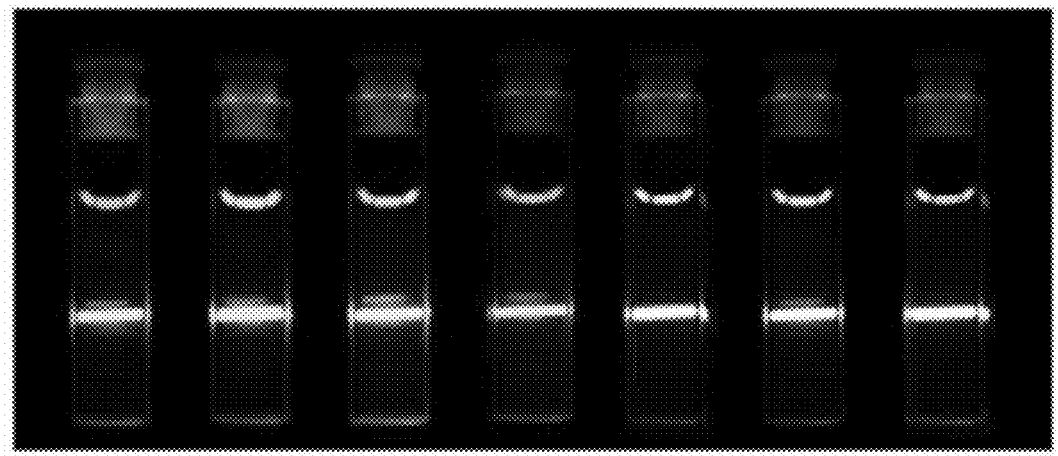
FIG. 4 shows (A) photograph of luminescence, and (B) corresponding Comission Internationale de l'Eclairage (International Commission on Illumination) (CIE) chromaticity color diagram, demonstrating ability of tuning emission colors using a method disclosed herein.
Figure 4:
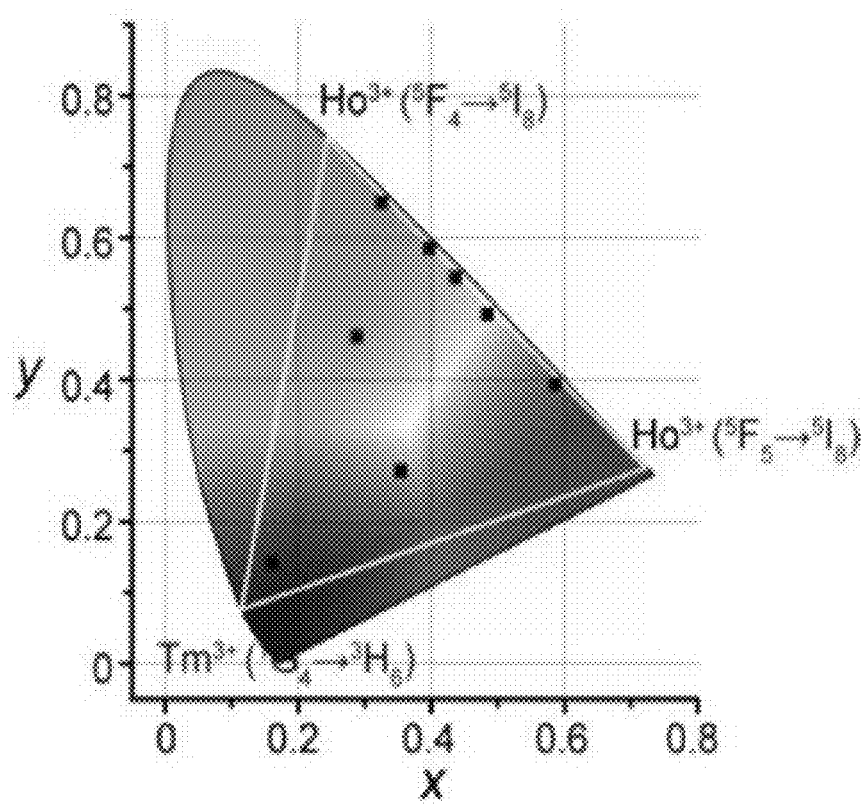
Figure 5:
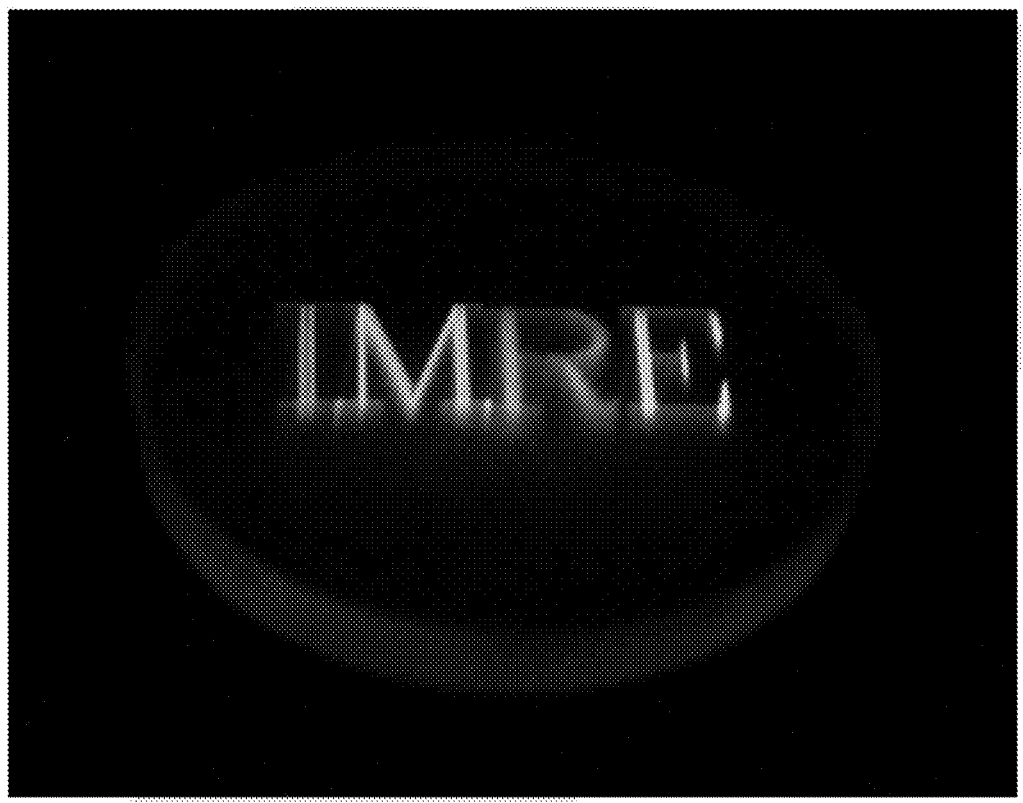
FIG. 5 shows a luminescent image of a three dimensional (3D) structure generated via computer-controlled near-infrared laser scanning from a polydimethylsiloxane (PDMS) sample containing nanoparticles according to an embodiment.
Figure 6:
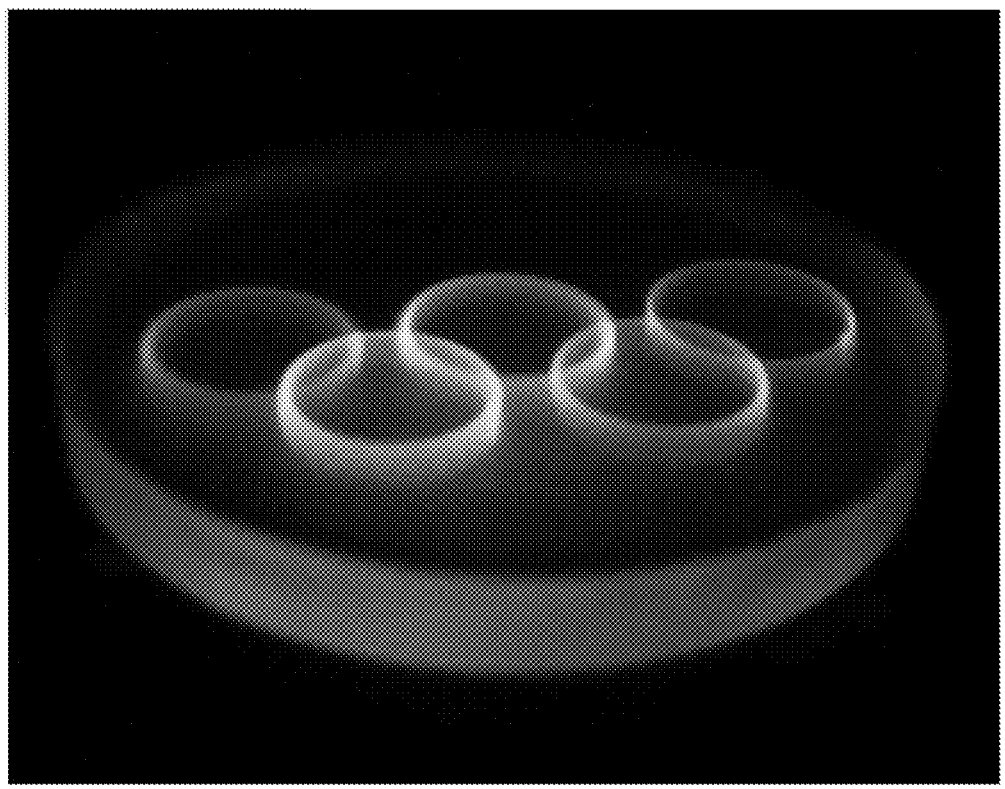
FIG. 6 shows a luminescent image of a 3D structure generated via computer-controlled near-infrared laser scanning from a PDMS sample containing nanoparticles according to an embodiment.

For example, radiation to the core-shell nanoparticle may be controlled so as to vary emission of primary light colors red (R), green (G), and blue (B), each having a characteristic wavelength range within the range of 380 nm to 780 nm, from the respective first layer and/or second layer of the shell of the core-shell nanoparticle. In so doing, secondary light colors such as orange, yellow, violet, or white may be derived through various combinations of red (R) and green (G) emissions from $Ho^{3+}$ and blue (B) emission from $Tm^{3+}$, such as that shown in FIG. 4.

The first activator and second activator may be present in their respective layers in amounts that are sufficiently high to allow energy transfer between the sensitizer to activator, while having concentrations that are sufficiently low to prevent concentration quenching, so as to provide luminescent centers in the core-shell nanoparticle.

In various embodiments, the first activator comprises or consists of $Tm^{3+}$. Amount of the first activator in the first layer may be in the range of about 0.1 mol % to about 1 mol %. For example, amount of the first activator in the first layer may be in the range of about 0.1 mol % to about 0.8 mol %, about 0.1 mol % to about 0.6 mol %, about 0.1 mol % to about 0.4 mol %, about 0.3 mol % to about 1 mol %, about 0.5 mol % to about 1 mol %, about 0.7 mol % to about 1 mol %, about 0.3 mol % to about 0.8 mol %, or about 0.4 mol % to about 0.6 mol %.

In various embodiments, the second activator comprises or consists of $Ho^{3+}$. Amount of the second activator in the second layer may be in the range of about 1 mol % to about 10 mol %. For example, amount of the second activator in the second layer may be in the range of about 1 mol % to about 8 mol %, about 1 mol % to about 6 mol %, about 1 mol % to about 4 mol %, about 3 mol % to about 10 mol %, about 5 mol % to about 10 mol %, about 7 mol % to about 10 mol %, about 2 mol % to about 8 mol %, about 3 mol % to about 6 mol %, or about 2 mol % to about 5 mol %.

As mentioned above, a first sensitizer may be present in the core of the core-shell nanoparticle to absorb incident photons, and the absorbed energy may be transferred through a series of steps resonantly to an activator present in the shell of the core-shell nanoparticle to emit the upconverted radiation. Although it is generally the case that the first activator is comprised in the first layer of the shell of the core-shell nanoparticle, in some embodiments, the first activator may also be present in the core of the core-shell nanoparticle. Accordingly, the first sensitizer that is present in the core of the core-shell nanoparticle may also absorb incident photons with transfer of the absorbed energy to the first activator that is present in the core of the core-shell nanoparticle. In such embodiments, amount of the first activator in the first layer specified above may refer to a total amount of the first activator in the first layer and in the core of the core-shell nanoparticle.

The second sensitizer and the third sensitizer present respectively in the first layer and the second layer may function in a similar manner as that of the first sensitizer, in that they may also absorb incident photons and resonantly transfer the absorbed energy to the first activator and second activator present respectively in the layers.

As in the case for the first sensitizer, the second sensitizer and the third sensitizer may be present in the metal fluoride in the form of ions. In various embodiments, the first sensitizer, the second sensitizer, and the third sensitizer are independently selected from the group consisting of $Yb^{3+}$, $Nd^{3+}$, and combinations thereof. The first sensitizer, the second sensitizer, and the third sensitizer may be the same or different. In various embodiments, the first sensitizer may comprise or consist of $Yb^{3+}$ and $Nd^{3+}$, the second sensitizer may comprise or consist of $Yb^{3+}$, and the third sensitizer may comprise or consist of $Yb^{3+}$.

In various embodiments, total amount of the first sensitizer in the core and the second sensitizer in the first layer may be in the range of about 5 mol % to about 40 mol %, such as in the range of about 5 mol % to about 30 mol %, about 5 mol % to about 20 mol %, about 5 mol % to about 10 mol %, about 10 mol % to about 40 mol %, about 20 mol % to about 40 mol %, about 30 mol % to about 40 mol %, about 10 mol % to about 30 mol %, or about 15 mol % to about 25 mol %.

The third sensitizer in the second layer may be present in an amount in the range of about 5 mol % to about 40 mol %, such as in the range of about 5 mol % to about 30 mol %, about 5 mol % to about 20 mol %, about 5 mol % to about 10 mol %, about 10 mol % to about 40 mol %, about 20 mol % to about 40 mol %, about 30 mol % to about 40 mol %, about 10 mol % to about 30 mol %, or about 15 mol % to about 25 mol %.

The first layer and the second layer of the shell may be arranged such that the first layer is nearer to the core of the core-shell nanoparticle than the second layer. In other words, starting from the core of the core-shell nanoparticle, and moving radially outwards, the first layer of the shell may be reached before the second layer. In alternate embodiments, the first layer and the second layer of the shell are arranged such that the second layer is nearer to the core of the core-shell nanoparticle than the first layer. This means that, starting from the core of the core-shell nanoparticle, and moving radially outwards, the second layer of the shell may be reached before the first layer.

In various embodiments, the first layer comprising the metal fluoride doped with the second sensitizer and the first activator may be disposed directly on the core of the core-shell nanoparticle. In so doing, the first layer of the shell may be in physical contact with the core of the core-shell nanoparticle with no intervening layers between the first layer and the core.

Thickness of the shell of the core-shell nanoparticle is not particularly limited and may be of a suitable size to render diameter of the core-shell nanoparticle to 100 nm or less. The first layer and the second layer comprised in the shell of the core-shell nanoparticle may be of the same or a different thickness to each other. In various embodiments, thickness of the shell of the core-shell nanoparticle may be in the range of about 3 nm to about 50 nm, such as about 10 nm to about 50 nm, about 20 nm to about 50 nm, about 30 nm to about 50 nm, about 3 nm to about 40 nm, about 3 nm to about 30 nm, about 3 nm to about 20 nm, about 10 nm to about 30 nm, about 20 nm to about 40 nm, or about 15 nm to about 35 nm.

The shell of the core-shell nanoparticle may further comprise at least one of a) a first passivating layer disposed between the first layer and the second layer, or b) a second passivating layer disposed on an outermost layer of the shell. The first passivating layer and the second passivating layer may comprise or be formed of the same metal fluoride as that of the core and/or shell of the core-shell nanoparticle. In contrast to the first layer and the second layer comprised in the shell of the core-shell nanoparticle, both of which may be considered as the active shell layers of the core-shell nanoparticle in that they contain sensitizers and/or activators which are responsible for optical signal generation from the core-shell nanoparticle, the first passivating layer and the second passivating layer are passive in that they do not contain sensitizers and/or activators and therefore do not give rise to an optical signal upon irradiation of radiation.

In various embodiments, the first passivating layer disposed between the first layer comprising the metal fluoride doped with the second sensitizer and the first activator and the second layer comprising the metal fluoride doped with the third sensitizer and the second activator functions to prevent cross-talk between the two active shell layers, referred to herein as an unwanted transfer of signals between the two active shell layers which may limit resulting resolution. Advantageously, this allows multicolor tuning such as in higher resolution for full-color emission from the core-shell nanoparticle.

In various embodiments, thickness of the first passivating layer is greater than 3 nm in order that the first passivating layer may sufficiently prevent cross-talk between the two active shell layers. For example, the first passivating layer may have a thickness in the range of about 3 nm to about 50 nm. For example, thickness of the first passivating layer may be in the range of about 3 nm to about 40 nm, such as about 3 nm to about 30 nm, about 3 nm to about 20 nm, about 3 nm to about 10 nm, about 10 nm to about 50 nm, about 20 nm to about 50 nm, about 30 nm to about 50 nm, about 10 nm to about 40 nm, or about 20 nm to about 30 nm.

A second passivating layer may be disposed on an outermost layer of the shell. Advantageously, by having a passivating layer disposed on an outermost layer of the shell, activator and sensitizer dopants in the shell may be separated from surface quenchers which may be present in the surrounding medium. As used herein, the term "surface quenchers" refer to entities that take away or deplete energy in the core-shell nanoparticles, which may otherwise be used to excite the activators. These may take the form of surrounding solutions, organic surfactants, and/or crystalline defects located on surface of the core-shell nanoparticles. Presence of surface quenchers may result in undesirable loss of energy from the excited activator ions to the surface quenchers, where excitation energy of the activator ions may be rapidly depleted. In arranging a passivating layer on an outermost layer of the shell, emission intensity of passivated nanoparticles may be one or two orders of magnitude higher than that of their non-passivated counterparts.

Depending on the arrangement of the first layer and the second layer of the shell with respect to the core of the core-shell nanoparticle, such as that mentioned above, either the first layer or the second layer may constitute an outermost layer of the shell.

In various embodiments, thickness of the second passivating layer is greater than 3 nm in order that the second passivating layer may sufficiently suppress quenching effects from luminescent quenchers which may be present in the surrounding medium or environment. For example, the second passivating layer may have a thickness in the range of about 3 nm to about 50 nm. For example, thickness of the second passivating layer may be in the range of about 3 nm to about 40 nm, such as about 3 nm to about 30 nm, about 3 nm to about 20 nm, about 3 nm to about 10 nm, about 10 nm to about 50 nm, about 20 nm to about 50 nm, about 30 nm to about 50 nm, about 10 nm to about 40 nm, or about 20 nm to about 30 nm.

In some embodiments, the first layer and/or the second layer of the shell may further comprise $Gd^{3+}$, $Ce^{3+}$, or their combination. For example, $Gd^{3+}$ and/or $Ce^{3+}$ may be co-doped in an active shell layer comprising $Ho^{3+}$ to promote red emission from $Ho^{3+}$.

In specific embodiments, a core-shell nanoparticle having a core comprising metal fluoride $NaYF_4$ doped with a first sensitizer of $Nd^{3+}$ and $Yb^{3+}$, and a shell having a first layer comprising $NaYF_4$ doped with a second sensitizer $Yb^{3+}$ and a first activator $Tm^{3+}$, and a second layer comprising $NaYF_4$ doped with a third sensitizer $Yb^{3+}$ and a second activator $Ho^{3+}$, is provided. The second layer may form an outermost layer of the shell. The core-shell nanoparticle may have a first passivating layer comprising $NaYF_4$ disposed between the first layer and the second layer, and a second passivating layer comprising $NaYF_4$ disposed on the second layer.

In a second aspect, a method of generating an optical signal is provided. The method comprises irradiating a core-shell nanoparticle according to the first aspect with radiation, and controlling at least one of a wavelength or a duration of the radiation to generate the optical signal from the core-shell nanoparticle.

Advantageously, embodiments disclosed herein allow emission of multiple colors from a single core-shell nanoparticle, in which a specific color for emission may be selected through varying the excitation conditions. The radiation may, for example, be from solar, ultraviolet (UV), visible and/or infrared (IR) energy. In various embodiments, the radiation is a pulsed or a continuous laser radiation.

The emission colors may be tuned using a pulsed diode laser with different pulse widths. For instance, a relatively long pulse (6 ms, 100 Hz) may produce a visible red emission from the core-shell nanoparticles. In contrast, a short pulse (200 µs, 100 Hz) may yield green emission from the core-shell nanoparticles. By tuning the excitation pulse widths in the range from about 10 ms to about 100 µs, light emission from the core-shell nanoparticles may be tuned to generate a multi-color emission.

The laser radiation may have a wavelength of 800 nm or 980 nm. For example, the radiation may be laser radiation from a 800 nm or 980 nm laser source. As mentioned above, $Yb^{3+}$ and $Nd^{3+}$ have large absorption cross sections, with $Yb^{3+}$ at 980 nm and $Nd^{3+}$ at 800 nm, which render their suitability for use as sensitizers. In irradiating the core-shell nanoparticles with laser radiation of these wavelengths, two or more photons may be sequentially absorbed to result in emission of a single photon having a higher energy (shorter wavelength) than the absorbed photons to result in the multi-color emission.

The multi-color emission may be in the form of an optical signal having one or more wavelengths in a range from about 380 nm to about 780 nm, such as about 380 nm to about 750 nm. For example, the color red may have a wavelength in the range of about 620 nm to about 750 nm, the color green may have a wavelength in the range of about 495 nm to about 570 nm, and the color blue may have a wavelength in the range of about 450 nm to about 495 nm. The colors red (R), green (G) and blue (B) constitute the primary colors of light, and secondary colors such as orange, yellow, violet, or white may be derived from various combinations of the primary colors to result in full-color emission. For example, the color orange may be derived from combining two wavelengths of red color and green color; the color yellow may be derived from combining two wavelengths of green color and blue color; the color violet may be derived from a combination of two wavelengths of red color and blue color; and the color white may be derived from combining wavelengths of red color, blue color, and green color.

By controlling at least one of a wavelength or a duration of the incident radiation on the core-shell nanoparticle, optical signals of different wavelengths, translating into light emissions of specific colors, may be generated from the core-shell nanoparticle.

Various embodiments refer in a third aspect to a method of preparing a core-shell nanoparticle.

The method includes providing a nanoparticle comprising a metal fluoride doped with a first sensitizer. Examples of suitable metal fluoride and first sensitizer have already been mentioned above.

In various embodiments, providing the nanoparticle comprising a metal fluoride doped with a first sensitizer includes (a) forming a reaction mixture comprising a first metal precursor and a solvent, (b) heating the reaction mixture under solvothermal conditions to form a complex of the first metal, and (c) adding the complex of the first metal to a solution comprising an alcohol, a fluorine precursor, and a second metal precursor, and heating the resultant mixture under solvothermal conditions to form the nanoparticle.

A first metal precursor as used in a method disclosed herein may be a compound such as a salt for providing the corresponding first metal in forming the nanoparticle. In various embodiments, the first metal comprises a metal of the metal fluoride and a metal of the first sensitizer. For example, the first metal may comprise one or more lanthanide elements. Examples of suitable lanthanide elements have already been mentioned above. The first metal precursor may, for example, be an inorganic salt such as a carbonate, or an organic salt such as an acetate, a stearate or an oleate of the corresponding metal. In various embodiments, the first metal precursor may be an acetate of a lanthanide element. In some embodiments, the first metal precursor is an acetate of a lanthanide selected from the group consisting of Y, Nd, Yb, Tm, Gd, Ce, or combinations thereof.

For example, when the metal fluoride is $NaYF_4$ and the first sensitizer is $Yb^{3+}$, the first metal may be a combination of Y and Yb. As a further example, when the metal fluoride is $NaYF_4$ and the first sensitizer is $Nd^{3+}$, the first metal may be a combination of Y and Nd.

The first metal precursor may be at least substantially dissolved in an aqueous medium such as water, prior to addition into the solvent to form the reaction mixture.

The solvent may comprise a non-polar solvent, which may be selected from the group consisting of decane, dodecane, tetradecane, hexadecane, octadecene, octadecane, trioctylphosphine oxide, mesitylene, and trichlorobenzene. In specific embodiments, the non-polar solvent comprises or consists of octadecene.

The solvent may further comprise a fatty acid, such as a $C_8$-$C_{18}$ organic carboxylic acid. Examples of a $C_8$-$C_{18}$ organic carboxylic acid include oleic acid, decanoic acid, dodecanoic acid, tetradecanoic acid, hexadecyl hexadecanoic acid, octodecanoic acid, or n-octanoic acid.

In specific embodiments, the solvent comprises or consists of a mixture of octadecene and oleic acid.

The reaction mixture comprising the first metal precursor and the solvent is heated under solvothermal conditions to form a complex of the first metal. As used herein, the term "solvothermal" refers generally to conditions of elevated pressure and often also elevated temperature involving a solvent. Accordingly, a solvent may be used above its boiling point, typically in an enclosed vessel that supports high pressures, such as a pressure reactor or an autoclave.

In various embodiments, methods disclosed herein may be carried out at an elevated pressure in the range of about 2 atm to about 100 atm, such as in the range of about 5 atm to about 100 atm, about 10 atm to about 100 atm, about 20 atm to about 80 atm, or about 15 atm to about 20 atm.

Due to the elevated pressure used, the reaction may be carried out at reaction temperatures that are significantly higher, e.g. 50° C., 100° C., 200° C. or 300° C. higher than the boiling point of the solvent used at atmospheric pressure. The reaction mixture may for instance be brought, e.g. warmed, to a temperature from about 50° C. to about 300° C., such as about 50° C. to about 300° C., about 100° C. to about 300° C., about 200° C. to about 300° C., about 150° C. to about 200° C. or about 100° C. to about 200° C.

A complex of the first metal may be formed. The complex formed may depend on the type of solvent used. In embodiments where a mixture of octadecene and oleic acid is used as the solvent, for example, the complex of the first metal may be a first metal-oleate complex. In specific embodiments wherein the first metal is a lanthanide element, the complex of the first metal is a lanthanide-oleate complex.

The method disclosed herein comprises adding the complex of the first metal to a solution comprising an alcohol, a fluorine precursor, and a second metal precursor, and heating the resultant mixture under solvothermal conditions to obtain the nanoparticle.

The alcohol may, for example, be a $C_1$-$C_6$ alcohol, such as methanol, ethanol, propanol, butanol, pentanol or hexanol. In specific embodiments, the alcohol comprises or consists of methanol.

The fluorine precursor may, for example, be selected from the group consisting of ammonium fluoride, sodium fluoride, and combinations thereof. In specific embodiments, the fluorine precursor comprises or consists of ammonium fluoride.

In various embodiments, the second metal comprises or consists of sodium. Accordingly, the second metal precursor may be selected from the group consisting of sodium hydroxide, sodium fluoride, sodium stearate, sodium oleate, and combinations thereof.

The resultant mixture is heated under solvothermal conditions to obtain the nanoparticle. Similar temperatures and/or pressures as that mentioned above for heating the reaction mixture comprising the first metal precursor and the solvent under solvothermal conditions to form a complex of the first metal may be used.

Once the reaction is complete or has reached a desired state, any further progress of the reaction may be stopped by removing the heat and allowing the formed mixture to cool down. The final product may be purified by centrifugation. After centrifugation, the precipitated products may be collected and dried to obtain a powder. Alternatively, the precipitated products may be re-dissolved in an organic solvent such as hexane for storage purposes.

The nanoparticle may constitute a core of the core-shell nanoparticle. The method to prepare the core-shell nanoparticle comprises forming a shell having a first layer comprising the metal fluoride doped with a second sensitizer and a first activator, and a second layer comprising the metal fluoride doped with a third sensitizer and a second activator on the nanoparticle. The first activator and the second activator are different, and each is independently selected from the group consisting of $Tm^{3+}$, $Ho^{3+}$, and combinations thereof.

Examples of suitable second sensitizer, third sensitizer, first activator, and second activator have already been mentioned above.

Forming the shell comprising the first layer and the second layer on the nanoparticle may be carried out using a similar method as that used to form the core of the core-shell nanoparticle, and using suitable materials of the second sensitizer, third sensitizer, first activator, and second activator.

For example, the nanoparticles forming a core of the core-shell nanoparticle may be added into a mixture containing a complex of the first metal, the second sensitizer and/or the first activator, so that the nanoparticles may function as seeds onto which the complex of the first metal, the second sensitizer and/or the first activator may be coated thereon. The first layer may be formed by epitaxial growth on the nanoparticle.

By subsequently subjecting the nanoparticles having the complex of first metal, the second sensitizer and/or the first activator coated thereon to a solution comprising an alcohol, a fluorine precursor, and a second metal precursor, and heating the resultant mixture under solvothermal conditions, a first layer comprising the metal fluoride doped with the second sensitizer and the first activator may be obtained.

Likewise, the nanoparticles having the first layer comprising the metal fluoride doped with the second sensitizer and the first activator may be added into a mixture containing a complex of the first metal, the third sensitizer and/or the second activator, so that the nanoparticles having the first layer comprising the metal fluoride doped with the second sensitizer and the first activator may function as seeds onto which the complex of the first metal, the third sensitizer and/or the second activator may be coated thereon.

By subsequently subjecting the nanoparticles having the complex of the first metal, the third sensitizer and/or the second activator coated thereon to a solution comprising an alcohol, a fluorine precursor, and a second metal precursor, and heating the resultant mixture under solvothermal conditions, a second layer comprising the metal fluoride doped with the second sensitizer and the first activator may be obtained.

Depending on the arrangement of the first layer and the second layer of the shell with respect to the core of the core-shell nanoparticle, such as that mentioned above, the above-mentioned sequence may be adapted to first form the second layer on the nanoparticle, followed by forming the first layer on the second layer.

The core-shell nanoparticle disclosed herein may be used as a biomarker in various applications such as deep-tissue labelling and/or imaging.

Advantageously, the core-shell nanoparticles disclosed herein have unique optical properties, such as narrow emission bandwidths, large anti-Stokes shifts, long luminescence lifetimes, and high photostability, make them more suitable as biomarkers than conventionally used organic dyes or quantum dots.

Hereinafter, the present invention will be described more fully with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, lengths and sizes of layers and regions may be exaggerated for clarity.

As used herein, the term "and/or" includes any and all combinations of one or more of the associated listed items. The invention illustratively described herein may suitably be practiced in the absence of any element or elements, limitation or limitations, not specifically disclosed herein. Thus, for example, the terms "comprising", "including", "containing", etc.

shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

In embodiments as disclosed herein, a novel nanostructured luminophore that is able to emit a wide range of visible colors with a single phosphor, otherwise termed herein as a luminescent material, has been developed. In this material, the emission color may be controlled by laser excitation. Different excitation lasers or laser pulses may result in variable emission colors. This technique may be useful in the development of multi-color emission probes, and which may particularly be useful for bioimaging applications.

In comparison with conventional phosphors in which one phosphor can only emit one color, the nanophosphor disclosed herein is able to emit different emission colors through control of laser excitation conditions. The emission color may be controlled not only by the excitation wavelength, but also by the excitation duration. Methods disclosed herein have demonstrated that tunable emission colors may be achieved using a single nanophosphor under a single excitation wavelength, by controlling excitation duration using a pulse excitation source. Emitting visible light under near-infrared light excitation via an upconversion process. The results shown are surprising, and run contrary to previous conceptions that emission color of phosphors may only be tuned by varying dopant compositions of the materials.

Example 1

Structure of Core-Shell Nanoparticles

The materials were based on a core-shell designed nanocrystal structure in which different lanthanide metal ions were precisely doped in specific core/shell layers. Using this strategy, different core/shell layers with different laser excitation source achieving emission of variable colors may be achieved from a single nanoparticle. The emission color may also be tuned by controlling the excitation durations and intensities.

Figure 2:
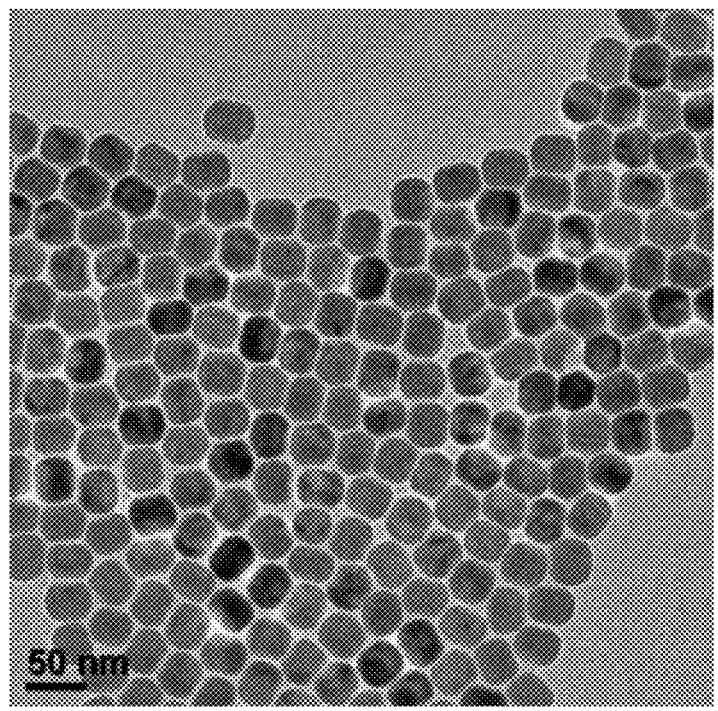
FIG. 2 shows a low-resolution transmission electron microscopy (TEM) image of a full-color emission upconversion nano-luminophore according to an embodiment. The nanocrystals includes a composition of $NaYF_4$ doped with $Nd^{3+}$, $Yb^{3+}$, $Tm^{3+}$, $Ho^{3+}$, $Ce^{3+}$, and/or $Gd^{3+}$ ions. Scale bar in the figure represents 50 nm.
Figure 3:
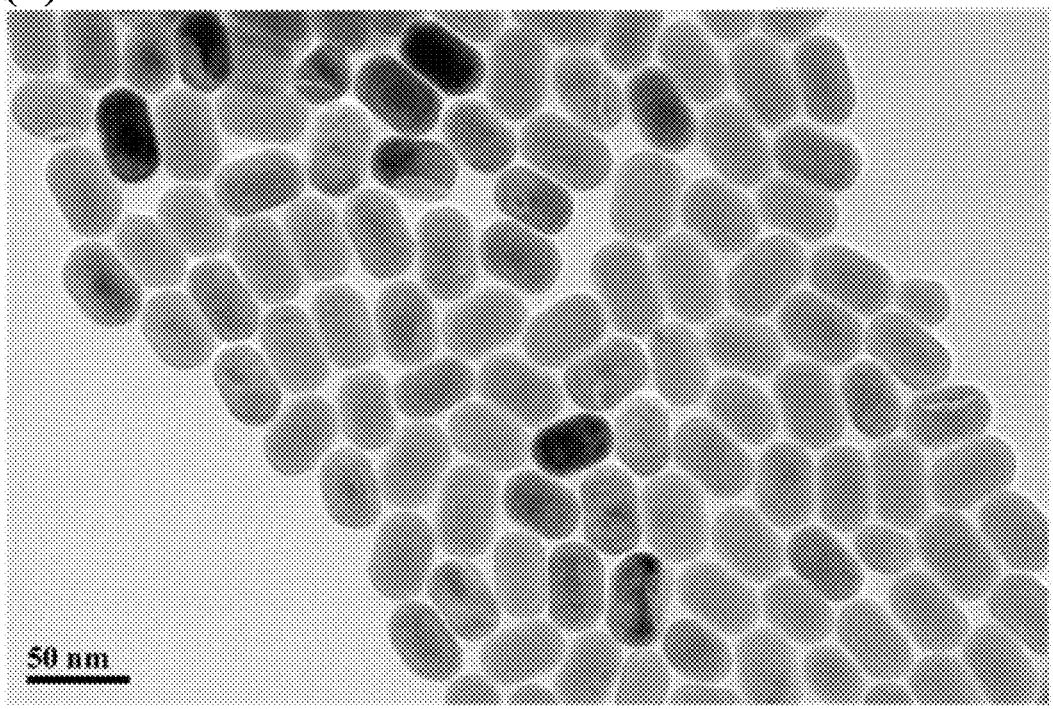
FIG. 3 shows (A) a low resolution TEM image of a typical core-shell full-color emission upconversion nano-luminophore indicating the uniform size distribution of the as prepared core-shell nanocrystals, and (B) a high resolution TEM image of the as-prepared core-shell full-color emission upconversion nano-luminophore showing the high crystallinity of the core-shell nanocrystals. Inset of (B) shows a corresponding indexed electron diffraction pattern of the nanocrystals in (B). Scale bar in (A) and (B) represents 50 nm and 10 nm, respectively.
Figure 3:
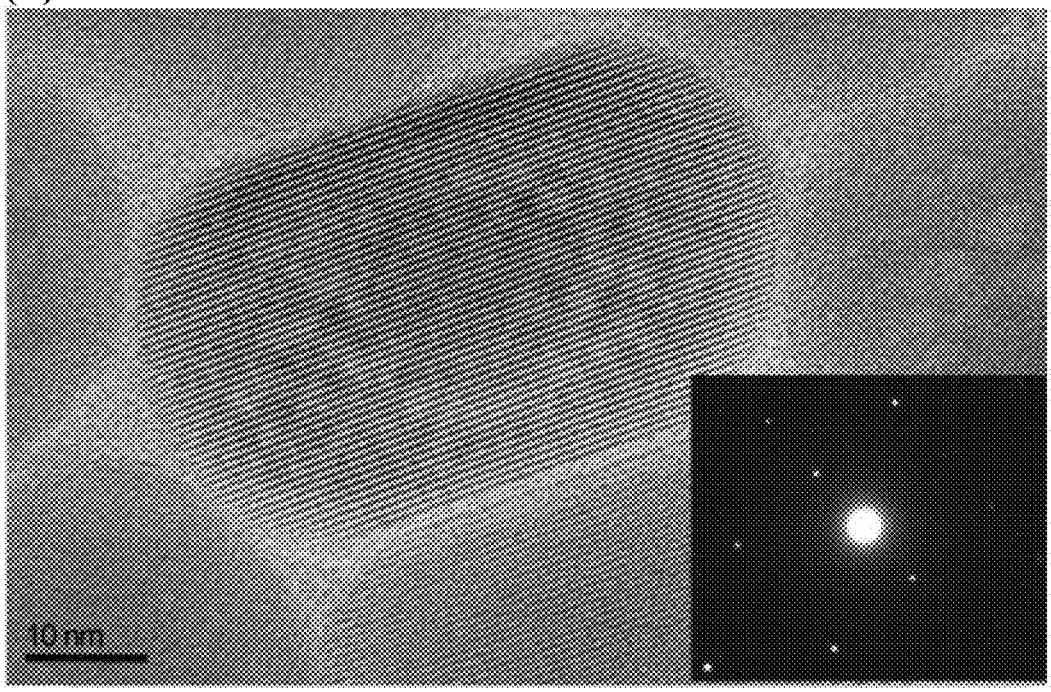

The nanostructured luminophore was based on the core-shell fluoride nanocrystals such as $NaYF_4$, $CaF_2$ or $NaGdF_4$. Specifically, multi-layer core-shell structured $NaYF_4$ nanoparticles were used (see FIG. 2). In these nanoparticles, lanthanide trivalent ions such as $Nd^{3+}$, $Yb^{3+}$, $Tm^{3+}$, $Ho^{3+}$, $Ce^{3+}$, and $Gd^{3+}$ were selectively doped in the core and shell layers of the nanoparticles. $Nd^{3+}$ or $Yb^{3+}$ was used to absorb the excitation energies from either 800 nm or 980 nm excitation laser sources. $Tm^{3+}$ was selectively doped for blue emission while $Ho^{3+}$ was used for green and red emissions.

The nanocrystals as demonstrated in embodiments disclosed herein contain a specific core-4-shell multilayers structure. Each layer was doped with different lanthanide dopants to realize the multiple emissions. Typically, 5 mol % to 40 mol % of $Nd^{3+}$ or $Yb^{3+}$ along with 0.1 mol % to 1 mol % $Tm^{3+}$ were doped in the core and the first shell layers. The second to the fourth shell layers were doped with 5 mol % to 40 mol % $Yb^{3+}$ along with 1 mol % to 10 mol % $Ho^{3+}$ and $Ce^{3+}$. In this case, the full-color emission was achieved through combinations of red (R), green (G) and blue (B) emissions with different intensity ratios by controlling the excitation durations, as well as the excitation wavelength of the laser excitation sources (see FIG. 4).

Example 2

Method of Preparing Core-Shell Nanoparticles

The core-shell nanoparticles were prepared by a solvent thermal method. Core nanoparticles were first prepared then shell layers were coated on the core nanoparticles through an epitaxial growth method.

In a typical experiment for synthesis of core nanoparticles, an aqueous solution (2 ml) containing amount of $Ln(CH_3CO_2)_3$ (0.4 mmol; Ln=Y, Nd, Yb, Tm, Gd, and/or Ce) was added into a mixture of oleic acid (3 ml) and 1-octadecene (7 ml) at room temperature. The mixture was heated at 150° C. for 1 hour to form lanthanide-oleate complexes.

Thereafter, the reaction solution was cooled down to room temperature followed by addition of a methanol solution (6 ml) containing NaOH (40 mg; 1 mmol) and $NH_4F$ (59.2 mg; 1.6 mmol). Subsequently, the mixture was heated at 50° C. for 30 min under vigorous stirring. The temperature was then increased to 100° C. to evaporate the methanol. After degassed for 10 minutes, the reaction mixture was heated to 290° C. at a heating rate of 10° C./min under an argon atmosphere. Upon completion of the reaction after 1.5 hour, the solution was cooled down to room temperature.

The resulting core nanocrystals were collected by centrifugation, washed with a mixture of cyclohexane and absolute ethanol for several times, and re-dispersed in cyclohexane (4 ml).

The procedure for preparing core-shell nanoparticles was identical to that for the synthesis of core nanoparticles. The only difference was that the core nanoparticles were added as seeds into a corresponding lanthanide-oleate precursor to induce a subsequently epitaxial growth of the additional shell layer. The resultant core-shell nanoparticles may be dispersed in organic solvents such as cyclohexane, or be kept as solid, and may be used directly for light excitation.

Potential applications of a core-shell nanoparticle disclosed herein include luminescence biomarkers for clinic diagnosis, bioimaging studies in laboratory works, sensing platforms for environmental monitoring, volumetric 3D display, and anticounterfeiting applications.

Advantages of embodiments disclosed herein include capability of simultaneous excitation by multiple light sources, high brightness, high photostability, wide color gamut and excellent color saturation, no auto-fluorescence and nonblinking, and low cost (scalable) and rewritable.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A core-shell nanoparticle having a core comprising a metal fluoride doped with a first sensitizer and a shell surrounding the core, wherein the shell comprises
   a) a first layer comprising the metal fluoride doped with a second sensitizer and a first activator, and
   b) a second layer comprising the metal fluoride doped with a third sensitizer and a second activator,
wherein the first activator and the second activator are different, and each is independently selected from the group consisting of $Tm^{3+}$, $Ho^{3+}$, and combinations thereof.

2. The core-shell nanoparticle according to claim 1, wherein the metal fluoride is selected from the group consisting of $NaYF_4$, $CaF_2$, $NaGdF_4$, $NaLuF_4$, and combinations thereof.

3. The core-shell nanoparticle according to claim 1, wherein the first sensitizer, the second sensitizer, and the third sensitizer are independently selected from the group consisting of $Yb^{3+}$, $Nd^{3+}$, and combinations thereof.

4. The core-shell nanoparticle according to claim 1, wherein the first sensitizer comprises at least one of $Yb^{3+}$ or $Nd^{3+}$.

5. The core-shell nanoparticle according to claim 1, wherein total amount of the first sensitizer in the core and the second sensitizer in the first layer is in the range of about 5 mol % to about 40 mol %.

6. The core-shell nanoparticle according to claim 1, wherein the first activator comprises $Tm^{3+}$.

7. The core-shell nanoparticle according to claim 6, wherein amount of the first activator in the first layer is in the range of about 0.1 mol % to about 1 mol %.

8. The core-shell nanoparticle according to claim 1, wherein the first layer is disposed directly on the core.

9. The core-shell nanoparticle according to claim 1, wherein the second activator comprises $Ho^{3+}$.

10. The core-shell nanoparticle according to claim 9, wherein amount of the second activator in the second layer is in the range of about 1 mol % to about 10 mol %.

11. The core-shell nanoparticle according to claim 1, wherein amount of the third sensitizer in the second layer is in the range of about 5 mol % to about 40 mol %.

12. The core-shell nanoparticle according to claim 1, wherein at least one of the first layer or the second layer further comprises $Gd^{3+}$, $Ce^{3+}$, or their combination.

13. The core-shell nanoparticle according to claim 1, wherein the shell further comprises at least one of a) a first passivating layer disposed between the first layer and the second layer, or b) a second passivating layer disposed on an outermost layer of the shell.

14. The core-shell nanoparticle according to claim 13, wherein the first passivating layer and the second passivating layer comprises the metal fluoride.

15. The core-shell nanoparticle according to claim 1, wherein the core further comprises the first activator.

16. A method of generating an optical signal, the method comprising
   a) irradiating a core-shell nanoparticle with radiation, the core-shell nanoparticle having a core comprising a metal fluoride doped with a first sensitizer and a shell surrounding the core, wherein the shell comprises
      i. a first layer comprising the metal fluoride doped with a second sensitizer and a first activator, and
      ii. a second layer comprising the metal fluoride doped with a third sensitizer and a second activator,
   wherein the first activator and the second activator are different, and each is independently selected from the group consisting of $Tm^{3+}$, $Ho^{3+}$, and combinations thereof; and
   b) controlling at least one of a wavelength or a duration of the radiation to generate the optical signal from the core-shell nanoparticle.

17. The method according to claim 16, wherein the radiation is a pulsed or a continuous laser radiation.

18. The method according to claim 17, wherein the laser radiation has a wavelength of about 800 nm or about 980 nm.

19. The method according to claim 16, wherein wavelength of the optical signal is one or more wavelengths in a range from about 380 nm to about 780 nm.

20. A method of preparing a core-shell nanoparticle, the method comprising
   a) providing a nanoparticle comprising a metal fluoride doped with a first sensitizer, and
   b) forming a shell having a first layer comprising the metal fluoride doped with a second sensitizer and a first activator and a second layer comprising the metal fluoride doped with a third sensitizer and a second activator on the nanoparticle,
wherein the first activator and the second activator are different, and each is independently selected from the group consisting of $Tm^{3+}$, $Ho^{3+}$, and combinations thereof.

* * * * *